United States Patent [19]

Fischer, deceased

[11] 4,140,517

[45] Feb. 20, 1979

[54] HERBICIDAL COMPOSITIONS

[75] Inventor: Adolf Fischer, deceased, late of Mutterstadt, Fed. Rep. of Germany, by Caecilia E. Fischer, heiress-at-law

[73] Assignee: BASF Aktiengesellschaft, Ludwigshafen, Fed. Rep. of Germany

[21] Appl. No.: 827,586

[22] Filed: Aug. 25, 1977

Related U.S. Application Data

[62] Division of Ser. No. 627,965, Nov. 3, 1975, Pat. No. 4,057,414.

[30] Foreign Application Priority Data

Nov. 18, 1974 [DE] Fed. Rep. of Germany ....... 2454576

[51] Int. Cl.² .......................... A01N 9/00; A01N 9/22; A01N 9/12; A01N 9/14

[52] U.S. Cl. .......................................... 71/88; 71/92; 71/100; 71/103

[58] Field of Search ....................... 71/92, 100, 103, 88

[56] References Cited

U.S. PATENT DOCUMENTS

| | | | |
|---|---|---|---|
| 3,095,299 | 6/1963 | Luckenbaugh | 71/100 |
| 3,175,897 | 3/1965 | Tilles et al. | 71/100 |
| 3,210,353 | 10/1965 | Reicheneder et al. | 71/92 |
| 3,330,642 | 7/1967 | Barron et al. | 71/100 |
| 3,330,643 | 7/1967 | Harman et al. | 71/100 |
| 3,810,751 | 5/1974 | Fischer | 71/92 |
| 3,826,642 | 7/1974 | Fischer | 71/92 |
| 3,870,740 | 3/1975 | Fischer et al. | 71/103 |
| 3,883,509 | 5/1975 | Fischer et al. | 71/91 |

*Primary Examiner*—Glennon H. Hollrah
*Attorney, Agent, or Firm*—Keil & Witherspoon

[57] ABSTRACT

Herbicides containing compositions of glycolic acid amides and other active ingredients.

5 Claims, No Drawings

HERBICIDAL COMPOSITIONS

This application is a division of application Ser. No. 627,965, filed Nov. 3, 1975, now U.S. Pat. No. 4,057,414, issued Nov. 8, 1977.

The present invention application relates to herbicides containing compositions of sulfonylglycolic acid amides or sulfonylglycolic acid imides.

It is known that pyridazones (German Pat. No. 1,105,232), benzofuranyl sulfonates (German Laid-Open Application DOS No. 1,926,139), benzofuranylalkylamino sulfonates (German Laid-Open Application DOS No. 2,324,592), azetidine carbothiolates (German Laid-Open Application DOS No. 2,312,045), fatty acids (German No. 959,066), thiol carbamates (U.S. Pat. No. 3,185,720; U.S. Pat. No. 3,330,821), carbamates (German Laid-Open Application DOS No. 1,567,151; German Printed Application DAS No. 1,137,255), pyrazolium compounds (German Laid-Open Application DOS No. 2,260,485), α-cyanoacrylates (German Laid-Open Application DOS No. 1,642,231), anilides (British No. 903,766) and 1,2,4-triazinones (German Laid-Open Application DOS No. 2,138,031) have a herbicidal action. However, this action is not always satisfactory.

We have now found that compositions of one or more of these active ingredients and sulfonylglycolic acid amides (German Laid-Open Applications DOS No. 2,201,432 and 2,334,715) or sulfonylglycolic acid imides (German Laid-Open Application DOS No. 2,219,923), which are known as individual herbicidal active ingredients, have an unforeseeably superior herbicidal action over their individual components.

These compositions consist of a. a glycolic acid amide of the formula $$X-\underset{\underset{O}{\parallel}}{C}-CH_2-Y,$$

where X denotes

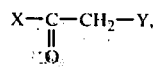

$R^1$ denoting alkyl, alkenyl, alkynyl, haloalkyl, haloalkenyl or haloalkynyl of a maximum of 6 carbon atoms, alkoxyalkyl, haloalkoxyalkyl, alkenoxyalkyl, alkynoxyalkyl or cycloalkyl, and $R^2$ denoting phenyl which may bear one or more identical or different substituents, the number of substituents, which may be halogen, lower alkyl of a maximum of 4 carbon atoms, haloalkyl, alkoxy, alkylsulfonyl, alkylaminosulfonyl, cyano, hydroxy, nitro or amino, being from 0 to 3, and the carbonamide nitrogen being a ring member of an optionally bicyclic cycloalkylimine which may be substituted by halogen or lower alkyl; which may contain further hetero atoms in the ring, and which has a maximum of 9 carbon atoms, and Y denotes

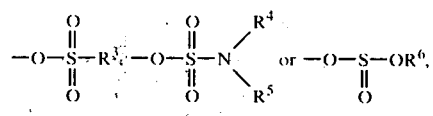

$R^3$, $R^4$, $R^5$ and $R^6$ denoting alkyl, alkenyl, alkynyl, haloalkyl, haloalkenyl or haloalkynyl of a maximum of 8 carbon atoms, unsubstituted or substituted phenyl or cycloalkyl of a maximum of 8 carbon atoms, and $R^4$ and $R^5$ additionally denoting hydrogen, and b. a pyridazone derivative of the formula

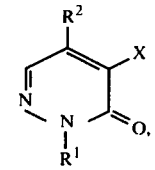

where X denotes chloro, bromo, iodo or methoxy, $R^1$ denotes phenyl which may be substituted by methyl, trifluoromethyl or halogen and $R^2$ denotes amino, α-hydroxy-β,β,β-trichloroethylamino, acetylamino, haloacetylamino, methoxy,

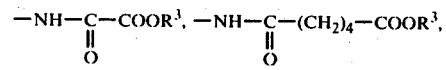

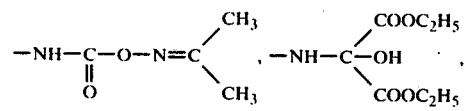

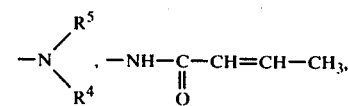

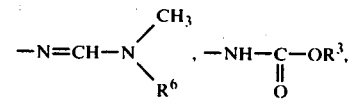

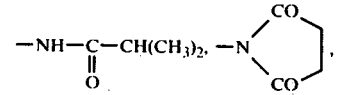

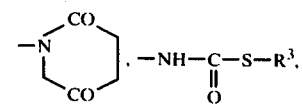

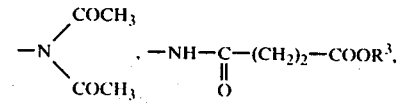

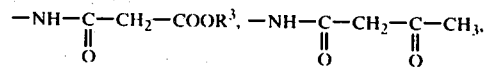

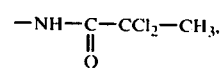

$R^3$ denoting hydrogen, a cation, a unsubstituted aliphatic amine, unsubstituted or halogen-substituted alkyl or alkenyl, unsubstituted or substituted phenyl or hydroxyethyl, $R^4$ denoting hydrogen, methyl, methoxy or ethyl, $R^5$ denoting methyl, ethyl or methoxy, and $R^6$ denoting hydrogen or methyl, and

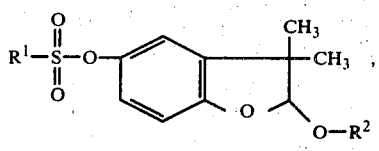

where R¹ denotes lower alkyl or the group

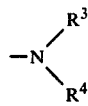

and R² denotes lower alkyl or has the same meanings as R³ and R⁴ when R¹ is

R³ and R⁴ denoting hydrogen or an unsubstituted or halogen- or alkoxy-substituted aliphatic radical of a maximum of 4 carbon atoms, or d. a benzofuranylalkylamino sulfonate of the formula

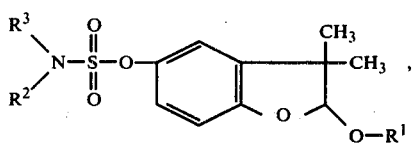

where R¹ denotes hydrogen, lower alkyl, alkenyl, alkynyl, haloalkyl, haloalkenyl, haloalkynyl, alkoxy, or radicals such as

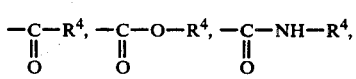

R⁴ denoting unsubstituted or halogen.

e. a thiol carbamate of the formula

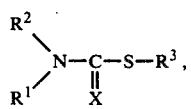

where R¹ denotes lower alkyl or an unsubstituted or methyl-substituted cycloaliphatic, bicycloaliphatic or tricycloaliphatic radical, R² denotes lower alkyl, alkenyl or alkynyl, R³ denotes unsubstituted or halogen-substituted alkyl, alkenyl or benzyl, and X denotes oxygen or sulfur.

Examples of suitable components for compositions according to the invention are the active ingredients listed below:

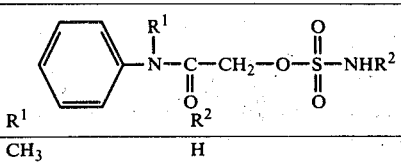

| R¹ | R² |
|---|---|
| CH₃ | H |

-continued

| R¹ | R² |
|---|---|
| CH₃ | CH₃ |
| CH₃ | C₂H₅ |
| CH₃ | CH₂CH₂Cl |
| CH₃ | n-C₃H₇ |
| CH₃ | i-C₃H₇ |
| CH₃ | n-C₄H₉ |
| CH₃ | sec-C₄H₉ |
| CH₃ | i-C₄H₉ |
| CH₃ | CH(C₂H₅)C₂H₅ |
| CH₃ | CH₂—CH(CH₃)C₂H₅ |
| CH₃ | CH—CH—(CH₂)₃—CH₃ with CH₃ CH₃ |
| C₂H₅ | CH₃ |
| C₂H₅ | C₂H₅ |
| C₂H₅ | CH₂CH₂Cl |
| C₂H₅ | n-C₃H₇ |
| C₂H₅ | i-C₃H₇ |
| n-C₃H₇ | CH₃ |
| n-C₃H₇ | i-C₃H₇ |
| C₂H₅ | H |
| i-C₃H₇ | H |
| i-C₃H₇ | CH₃ |
| i-C₃H₇ | C₂H₅ |
| i-C₃H₇ | CH₂CH₂Cl |
| i-C₃H₇ | n-C₃H₇ |
| i-C₃H₇ | i-C₃H₇ |
| i-C₃H₇ | n-C₄H₉ |
| i-C₃H₇ | sec-C₄H₉ |
| i-C₃H₇ | cyclohexyl |
| CH₂—CH=CH₂ | CH₃ |
| CH₂—C≡CH | CH₃ |
| CH₂—C≡CH | i-C₃H₇ |
| n-C₄H₉ | CH₃ |
| n-C₄H₉ | C₂H₅ |
| n-C₄H₉ | n-C₃H₇ |
| n-C₄H₉ | i-C₃H₇ |
| sec.-C₄H₉ | H |
| sec.-C₄H₉ | CH₃ |
| sec.-C₄H₉ | C₂H₅ |
| sec.-C₄H₉ | CH₂CH₂Cl |
| sec.-C₄H₉ | n-C₃H₇ |
| sec.-C₄H₉ | i-C₃H₇ |
| i-C₄H₉ | i-C₃H₇ |
| tert.-C₄H₉ | CH₃ |
| tert.-C₄H₉ | C₂H₅ |
| tert.-C₄H₉ | CH₂CH₂Cl |
| tert.-C₄H₉ | i-C₃H₇ |
| CH₃ | H |
| CH—C≡CH \| CH₃ | CH₃ |
| CH—C≡CH \| CH₃ | C₂H₅ |
| CH—C≡CH \| CH₃ | CH₂CH₂Cl |
| CH—C≡CH \| CH₃ | n-C₃H₇ |
| CH—C≡CH \| CH₃ | i-C₃H₇ |
| CH—C≡CH \| CH₃ | n-C₄H₉ |
| CH—C≡CH \| CH₃ | i-C₃H₇ |
| CH—CH=CH₂ | |

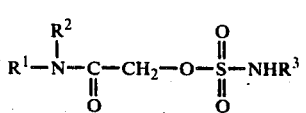

| R¹ | R² | R³ |
|---|---|---|

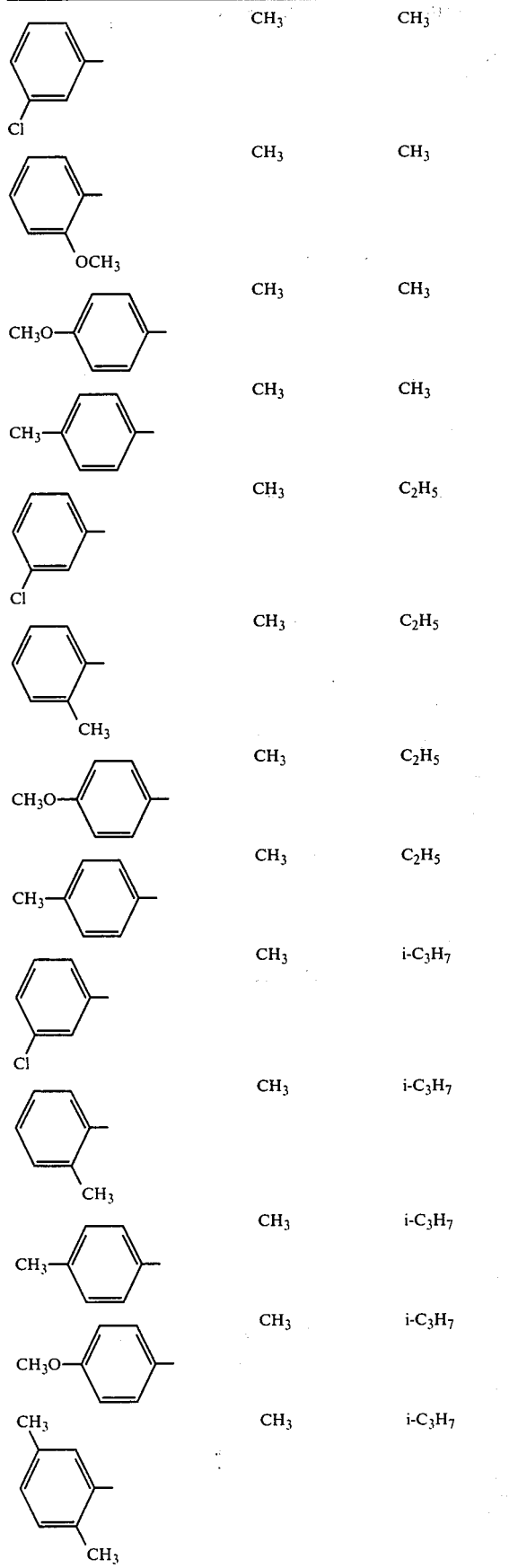
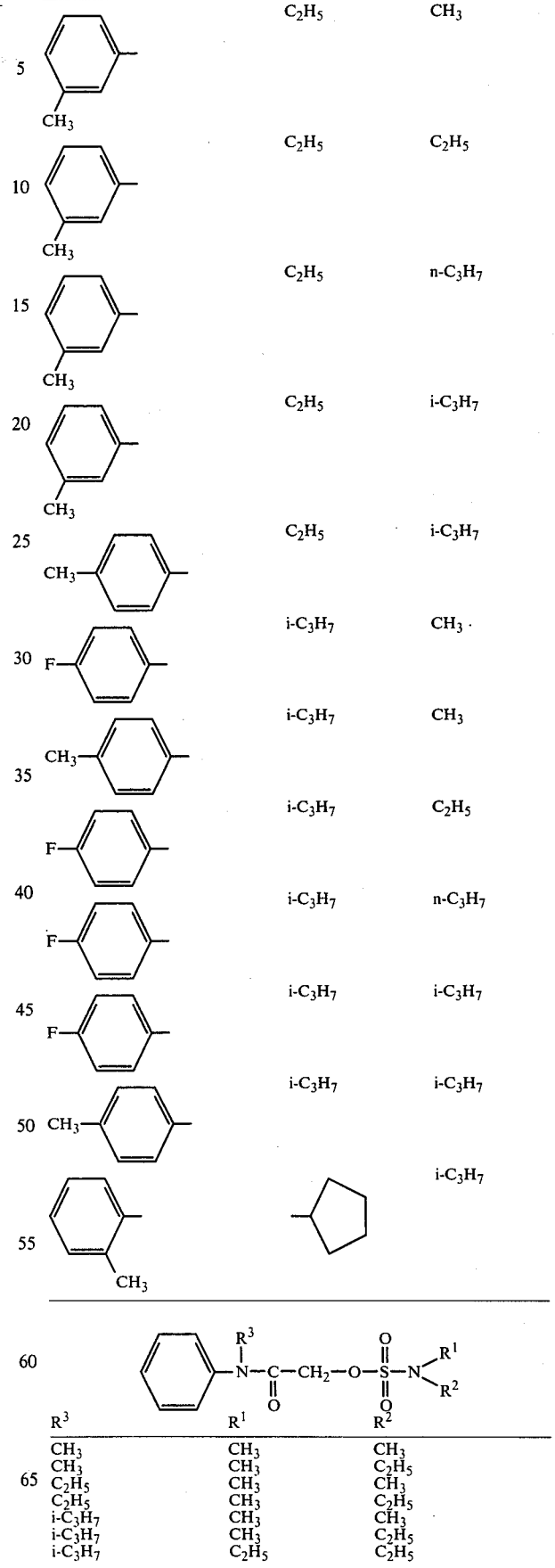

| | -continued | |
|---|---|---|
| i-C$_3$H$_7$ | CH$_3$ | CH$_2$CH$_2$Cl |
| sec-C$_4$H$_9$ | CH$_3$ | CH$_3$ |

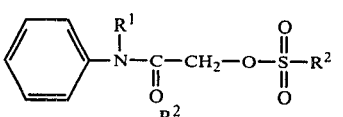

| R$^1$ | R$^2$ |
|---|---|
| CH$_2$—C≡CH | CH$_3$ |
| i-C$_3$H$_7$ | C$_2$H$_5$ |
| i-C$_3$H$_7$ | n-C$_3$H$_7$ |
| i-C$_3$H$_7$ | i-C$_3$H$_7$ |
| i-C$_3$H$_7$ | n-C$_4$H$_9$ |
| tert-C$_4$H$_9$ | CH$_3$ |
| sec-C$_4$H$_9$ | CH$_3$ |
| i-C$_4$H$_9$ | CH$_3$ |
| CH$_3$-CH-CH=CH$_2$ | CH$_3$ |
| CH$_3$-CH-C≡CH | CH$_3$ |
| CH$_3$-CH-C≡CH | C$_2$H$_5$ |
| CH$_3$-CH-C≡CH | n-C$_3$H$_7$ |
| CH$_3$-CH-C≡CH | i-C$_3$H$_7$ |
| CH$_3$-CH-C≡CH | n-C$_4$H$_9$ |
| CH$_3$-CH-C≡CH | phenyl |
| CH$_3$-CH-C≡CH | p-tolyl |
| i-C$_3$H$_7$ | CH$_3$ |
| (CH$_3$)$_2$C(C≡CH)- | CH$_3$ |

Structure: R$^1$R$^2$N-C(=O)-CH$_2$-O-SO$_2$-R$^3$

| R$^1$ | R$^2$ | R$^3$ |
|---|---|---|
| 2,6-(CH$_3$)$_2$-phenyl | —CH$_2$OCH$_3$ | CH$_3$ |
| 2-CH$_3$,6-C$_2$H$_5$-phenyl | —CH$_2$—OCH$_3$ | CH$_3$ |
| 2,6-(C$_2$H$_5$)$_2$-phenyl | CH$_2$—OCH$_3$ | CH$_3$ |
| 2,6-(C$_2$H$_5$)$_2$-phenyl | CH$_2$—OCH$_3$ | CH$_2$Cl |
| 2,6-(C$_2$H$_5$)$_2$-phenyl | CH$_2$—OCH$_3$ | C$_2$H$_5$ |
| 2,6-(C$_2$H$_5$)$_2$-phenyl | CH$_2$—OCH$_3$ | i-C$_3$H$_7$ |
| 2,6-(i-C$_3$H$_7$)$_2$-phenyl | CH$_2$—OCH$_3$ | CH$_3$ |
| 2,6-(i-C$_3$H$_7$)$_2$-phenyl | CH$_2$—OCH$_3$ | C$_2$H$_5$ |
| 2,6-(CH$_3$)$_2$-phenyl | CH$_2$—OC$_2$H$_5$ | CH$_3$ |
| 2-CH$_3$,6-C$_2$H$_5$-phenyl | CH$_2$—OC$_2$H$_5$ | CH$_3$ |
| 2-CH$_3$,6-C$_2$H$_5$-phenyl | CH$_2$—OC$_2$H$_5$ | C$_2$H$_5$ |
| 2-CH$_3$,6-C$_2$H$_5$-phenyl | —CH$_2$—OC$_2$H$_5$ | i-C$_3$H$_7$ |
| 2,6-(C$_2$H$_5$)$_2$-phenyl | CH$_2$—OC$_2$H$_5$ | CH$_3$ |
| 2-CH$_3$,6-C$_2$H$_5$-phenyl | —CH$_2$OC$_2$H$_5$ | CH$_2$—CH(CH$_3$)$_2$ |
| 2-CH$_3$,6-C$_2$H$_5$-phenyl | CH$_2$—OC$_3$H$_7$n | CH$_3$ |
| 2,6-(CH$_3$)$_2$-phenyl | CH$_2$—OC$_3$H$_7$n | C$_2$H$_5$ |
| 2,6-(CH$_3$)$_2$-phenyl | CH$_2$—O—CH(CH$_3$)$_2$ | C$_2$H$_5$ |

-continued

| | | |
|---|---|---|
| 2,3-(CH3)2-C6H3- | CH2-O-CH(CH3)-C2H5 | C2H5 |
| 2,3-(CH3)2-C6H3- | CH2-O-CH(CH3)2 | CH3 |
| 2-CH3-3-C2H5-C6H3- | CH2-O-CH(CH3)-C2H5 | CH3 |
| 2-CH3-3-C2H5-C6H3- | CH2-O-C3H7n | CH3 |
| 2-CH3-3-C2H5-C6H3- | CH2-O-CH(CH3)2 | CH3 |
| 2,3-(C2H5)2-C6H3- | CH2-OC3H7n | CH3 |
| 2,3-(C2H5)2-C6H3- | CH2-O-CH2-CH=CH2 | CH3 |
| 2,3-(CH3)2-C6H3- | -CH2-O-CH2-C≡CH | CH3 |
| 2,3-(C2H5)2-C6H3- | CH2-O-CH(CH3)2 | CH3 |
| 2,3-(CH3)2-C6H3- | -CH2-O-CH(CH3)-C2H5 | CH3 |
| 2-CH3-3-C2H5-C6H3- | CH2-O-C(CH3)3 | CH3 |
| 2,3-(CH3)2-C6H3- | -CH2-O-CH(CH3)-C2H5 | C2H5 |
| 2,3-(CH3)2-C6H3- | CH2-O-CH2-CH=CH2 | CH3 |

-continued

| 2,3-(CH3)2-C6H3- | CH2-O-CH2-CH(CH3)2 | CH3 |

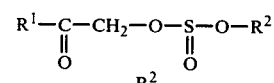

| R | n |
|---|---|
| CH3 | 4 |
| C2H5 | 4 |
| CH2CH2Cl | 4 |
| i-C3H7 | 4 |
| n-C3H7 | 4 |
| n-C4H9 | 4 |
| sec.-C4H9 | 4 |
| i-C4H9 | 4 |
| CH3 | 5 |
| C2H5 | 5 |
| n-C3H7 | 5 |
| i-C3H7 | 5 |
| n-C4H9 | 5 |
| CH3 | 6 |
| C2H5 | 6 |
| CH2CH2Cl | 6 |
| n-C3H7 | 6 |
| i-C3H7 | 6 |
| n-C4H9 | 6 |
| sec.-C4H9 | 6 |
| CH(C2H5)2 | 6 |
| CH2-CH(CH3)C2H5 | 6 |
| CH3 | 7 |
| C2H5 | 7 |
| i-C3H7 | 7 |
| n-C3H7 | 7 |
| -CH2-CH2-Cl | 7 |
| H | 8 (bicyclo) |
| CH3 | 8 (bicyclo) |
| C2H5 | 8 (bicyclo) |
| i-C3H7 | 8 (bicyclo) |
| n-C3H7 | 8 (bicyclo) |
| n-C4H9 | 8 (bicyclo) |
| sec.-C4H9 | 8 (bicyclo) |
| i-C4H9 | 8 (bicyclo) |

$$R^1-C(=O)-CH_2-O-S(=O)_2-O-R^2$$

| R1 | R2 |
|---|---|
| (azepan-1-yl) | CH3 |
| " | C2H5 |
| " | n-C3H7 |
| " | i-C3H7 |
| " | n-C4H9 |
| " | CH2-CH=CH2 |
| " | i-C3H7 |
| (2-methyl-azepan-1-yl) | C2H5 |
| | CH3 |
| (3-methyl-azepan-1-yl) | |
| " | C2H5 |
| " | i-C3H7 |
| | C2H5 |
| (4-methyl-azepan-1-yl) | |
| " | i-C3H7 |

| | | |
|---|---|---|
| 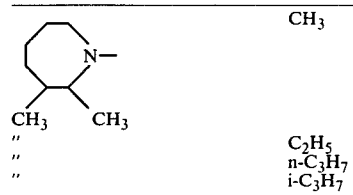 | CH₃ | |
| " | C₂H₅ | |
| " | n-C₃H₇ | |
| " | i-C₃H₇ | |

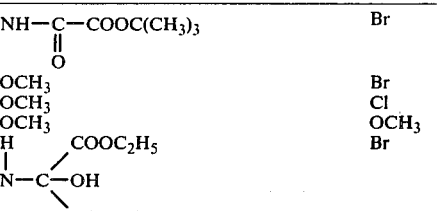

| R¹ | R² | X |
|---|---|---|
|  | NH₂ | Cl |
| " | NH₂ | Br |
| " | NH—CHOHCCl₃ | Br |
| " | NH—C(O)—CH₃ | Cl |
| " | NH—C(O)—CH₃ | Br |
| " | NH—C(O)—CH₂Br | Br |
| " | NH—C(O)—CH₂Cl | Br |
| " | NH—C(O)—CHCl₂ | Br |
| " | NH—C(O)—CH₂—C(O)—CH₃ | Br |
| " | NH—C(O)—COONa | Br |
| " | NH—C(O)—COOCH₃ | Br |
| " | NH—C(O)—COOC₂H₅ | Br |
| " | NH—C(O)—COOCH(CH₃)₂ | Br |
| " | NH—C(O)—COOC(CH₃)₃ | Br |
| " | NH—C(O)—COOC₆H₅ | Br |
| " | NH—C(O)—COOH · N(CH₃)(C₂H₄OH)(CH₃) | Br |
| " | OCH₃ | Cl |
| " | OCH₃ | Br |
| " | OCH₃ | OCH₃ |
| " | NH—C(O)—(CH₂)₄—COOCH₃ | Br |
| " | NH—C(O)—COOCH₂—CCl=CCl₂ | Br |
| " | NH—COON=C(CH₃)(CH₃) | Br |
| 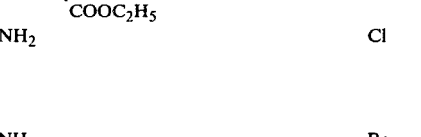 | NH₂ | Cl |
| " | NH₂ | Br |
| " | NH—C(O)—COOC(CH₃)₃ | Br |
| " | OCH₃ | Br |
| " | OCH₃ | Cl |
| " | OCH₃ | OCH₃ |
| " | N(H)(C(COOC₂H₅)(OH)(COOC₂H₅)) | Br |
| 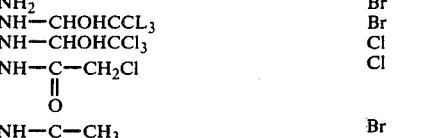 | NH₂ | Cl |
| " | NH₂ | Br |
| " | NH—CHOHCCl₃ | Br |
| " | NH—CHOHCCl₃ | Cl |
| " | NH—C(O)—CH₂Cl | Cl |
| " | NH—C(O)—CH₃ | Br |
| " | N(C₂H₅)(C₂H₅) | Cl |
| " | NHC₂H₅ | Cl |
| " | NH—C(O)—COOC₂H₅ | Br |
| " | NH—C(O)—COOH | Br |
| " | NH—C(O)—CHCl₂ | Br |
| " | N=CH—N(CH₃)(CH₃) | Br |
| " | N(CH₃)(OCH₃) | Cl |
| " | N(CH₃)(CH₃) | Cl |
| " | N(CH₃)(CH₃) | Br |
| " | NHCH₃ | Cl |
| " | NHCH₃ | Br |
| " | OCH₃ | Cl |
| " | OCH₃ | Br |
| " | OCH₃ | OCH₃ |
| " | NH—OCH₃ | Cl |
| " | NH₂ | Br |
| 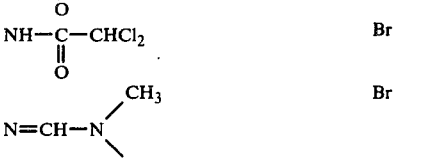 | | |
| " | NH—CHOH—CCl₃ | Cl |
| " | NH₂ | Cl |
| " | OCH₃ | OCH₃ |
| " | OCH₃ | Br |
| " | OCH₃ | OCH₃ |
| 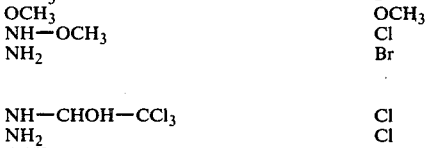 | | |
| " | OCH₃ | OCH₃ |
|  | | |
| | OCH₃ | OCH₃ |
|  | | |

-continued

| | | |
|---|---|---|
| 3-Br-C6H4- | OCH3 | OCH3 |
| C6H5- | NH2 | J |
| " | OCH3 | J |
| " | NH—C(=O)—CH2Cl | J |
| " | NH—C(=O)—COOC2H5 | J |
| " | NH—C(=O)—CH=CH—CH3 | Cl |
| " | NH—C(=O)—CH(CH3)2 | Br |
| " | NH—C(=O)—O—CH2—CH2OH | Cl |
| " | N(CO)2CH=CH (maleimide) | Cl |
| " | N(CO)2CH2CH2 (succinimide) | Br |
| " | NH—CHOHCCl3 | Cl |
| " | NH—C(=O)—CH2Cl | Cl |
| " | N=CH—NHCH3 | Br |
| " | N=CH—NH—CH3 | Cl |
| " | N=CH—N(CH3)2 | Br |
| " | NH—COSC2H5 | Cl |
| " | N(COCH3)2 | Br |
| " | NH—C(=O)—(CH2)2COCH3 | Cl |
| " | NH—C(=O)—CH2—COOC2H5 | Br |
| " | NH—C(=O)—CCl2—CH3 | Br |
| " | NH—C(=O)—CCl3 | Br |

$$\begin{array}{c}R^2\\ \diagdown\\ N-C-S-R^3\\ \diagup\quad \|\\ R^1\quad O\end{array}$$

| R¹ | R² | R³ |
|---|---|---|
| i-C3H7 | i-C3H7 | CH2—CCl=CHCl |
| i-C3H7 | i-C3H7 | CH2—CCl=CCl2 |
| n-C3H7 | n-C3H7 | C2H5 |
| i-C4H9 | i-C4H9 | C2H5 |
| n-C4H9 | C2H5 | n-C3H7 |
| n-C3H7 | n-C3H7 | n-C3H7 |
| n-C3H7 | n-C3H7 | tert.-C4H9 |
| C2H5 | C2H5 | —CH2—C6H4—Cl |
| cyclohexyl | C2H5 | C2H5 |
| indanyl | C2H5 | C2H5 |
| " | C2H5 | CH3 |
| " | C2H5 | i-C3H7 |
| " | C2H5 | C2H5 |
| norbornyl | C2H5 | C2H5 |
| 2-methylcyclohexyl | C2H5 | C2H5 |
| cyclohexyl | CH2—CH=CH2 | C2H5 |
| " | CH2—C≡CH | C2H5 |
| " | CH2—C≡C—CH3 | C2H5 |
| C2H5 | C2H5 | N—C(=S)—S—CH2—CCl=CH2 |

$$\begin{array}{c}R^2\\ \diagdown\\ N-C-O-R^3\\ \diagup\quad \|\\ R^1\quad O\end{array}$$

Sulfurous acid esters of glycolic acid amides, azetidine carbothioates and butynyl carbamates may also be used as components in addition to the active ingredients listed above.

The sulfurous acid esters of glycolic acid amides (a) may be obtained by reacting a glycolic acid amide with an alkyl chlorosulfinate at 10° to 15° C. in an inert solvent and in the presence of an agent capable of binding hydrogen chloride.

For instance, O-ethyl-O-(1-carbonylmethylazacycloheptane)-sulfite may be prepared by dripping a solution of 12.9 parts by weight of ethyl chlorosulfinate in 50 parts by weight of benzene at 10° to 15° into 15.7 parts by weight of glycolic acid hexamethylene amide dissolved together with 8 parts by weight of pyridine in 50 parts by weight of dry benzene. After 30 minutes the precipitated pyridinium hydrochloride is filtered off and the organic phase washed with water. After drying has been effected, the benzene is distilled off. There is obtained 20.4 parts by weight of the desired product. The compound has the following structure:

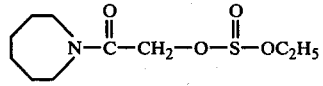

$n_{25} = 1.4910$.

The following active ingredients may for example be used:

N-methylacetanilido-(α-ethylsulfite)
N-methylacetanilido-(α-isopropylsulfite)
N-(butyn-1-yl-3)-acetanilido-(α-ethylsulfite)
N-(butyn-1-yl-3)-acetanilido-(α-isopropylsulfite)
N-(butyn-1-yl-3)-acetanilido-(α-methylsulfite) m.p.: 69° to 70° C.
N-isopropylacetanilido-(α-methylsulfite) m.p.: 60° to 61° C.
N-ethylacetanilido-(α-propylsulfite) $n_{25}^D$: 1.5295
N-ethylacetanilido-(α-isopropylsulfite) $n_{25}^D$: 1.5164
N-ethylacetanilido-(α-methylsulfite) $n_{25}^D$: 1.5118
N-ethylacetanilido-(α-ethylsulfite) $n_{25}^D$: 1.5010

N-methyl-(4-methoxyacetanilido)-(α-isopropylsulfite)
N-(butyn-1-yl-3)-(4-methoxyacetanilido)-(α-isopropylsulfite)
N-methyl-(p-methylacetanilido)-(α-isopropylsulfite)
N-butyn-1-yl-3)-(p-methylacetanilido)-(α-isopropylsulfite)
N-(2-methylbenzyl)-acetanilido-(α-methylsulfite)
N-(2-methylbenzyl)-acetanilido-(α-ethylsulfite)
N-(2-methylbenzyl)-acetanilido-(α-propylsulfite)
N-(2-methylbenzyl)-acetanilido-(α-isopropylsulfite)
N-tert-butylacetanilido-(α-isopropylsulfite) m.p.: 78° C.
N-tert-butylacetanilido-(α-methylsulfite) m.p.: 57° C.
N-methylacetanilido-(α-sec-butylsulfite), $n_{25}$ = 1.5083
N-(butyn-1-yl-3)-acetanilido-(α-isobutylsulfite) $n_{25}$: 1.5098
N-(butyn-1-yl-3)-acetanilido-(α-sec-butylsulfite) $n_{25}$: 1.5132
N-(butyn-1-yl-3)-acetanilido-(α-n-butylsulfite) $n_{25}$: 1.5172
N-isobutylacetanilido-(α-methylsulfite) $n_{25}$: 1.5229
N-isobutylacetanilido-(α-ethylsulfite) $n_{25}$: 1.5100
N-methylacetanilido-(α-n-butylsulfite) $n_{25}$: 1.5144
N-isobutylacetanilido-(α-propylsulfite) $n_{25}$: 1.5059
N-isobutylacetanilido-(α-isopropylsulfite) $n_{25}$: 1.5028
N-methylacetanilido-(α-methylsulfite)
N-methylacetanilido-(α-isobutylsulfite)
N-(buty-1-yl-3)-acetanilido-(α-methylsulfite)
N-methyl-(2-methylacetanilido)-(α-methylsulfite)
N-methyl-(4-methylacetanilido)-(α-methylsulfite)
N-methyl-(4-methoxyacetanilido)-(α-methylsulfite)
N-methyl-(3-chloroacetanilido)-(α-methylsulfite)
N-methyl-(2-methylacetanilido)-(α-ethylsulfite)
N-methylacetanilido-[α-(1-methyl-2-methoxy)-ethylsulfite]
N-methyl-(4-methylacetanilido)-(α-ethylsulfite)
N-methyl-(4-methoxyacetanilido)-(α-ethylsulfite)
N-methyl-(3-chloroacetanilido)-(α-ethylsulfite)
N-methyl-(2-methylacetanilido)-(α-isopropylsulfite)
N-methyl-(3-chloroacetanilido)-(α-isopropylsulfite)
N-methyl-(4-methylacetanilido)-(α-n-butylsulfite)
O-methyl-O-(1-carbonylmethylazacycloheptane)-sulfite; $n_{25}$ = 1.4955
O-isopropyl-O-(1-carbonylmethylazacycloheptane)-sulfite; $n_{25}$ = 1.4695
O-butyl-O-(1-carbonylmethylazacycloheptane)-sulfite; $n_{25}$ = 1.4875
O-propyl-O-(1-carbonylmethylazacycloheptane)-sulfite; $n_{25}$ = 1.4828
O-isopropyl-O-(1-carbonylmethylazacycloheptane)-sulfite; m.p. = 58° to 59° C.
O-ethyl-O-(1-carbonylmethyl-2-methylazacycloheptane)-sulfite; $n_{25}$ = 1.4882
O-isopropyl-O-(1-carbonylmethyl-2-methylazacycloheptane)-sulfite; $n_{25}$ = 1.4740
O-methyl-O-(1-carbonylmethyl-2,3-dimethylazacycloheptane)-sulfite; $n_{25}$ = 1.4952
O-ethyl-O-(1-carbonylmethyl-2,3-dimethylazacycloheptane)-sulfite; $n_{25}$ = 1.4860
O-propyl-O-(1-carbonylmethyl-2,3-dimethylazacycloheptane)-sulfite; $n_{25}$ = 1.4849
O-isopropyl-O-(1-carbonylmethyl-2,3-dimethylazacycloheptane)-sulfite; $n_{25}$ = 1.4749
O-ethyl-O-(1-carbonylmethyl-3,5,5-trimethyl-(3,3,5-trimethyl)-azacycloheptane)-sulfite; $n_{25}$ = 1.4850
(1:1 isomer mixture of the 3,3,5- and 3,5,5-trimethyl derivative)
O-isopropyl-O-(1-carbonylmethyl-3-methyl-(2-methyl)-azacycloheptane)-sulfite; $n_{25}$ = 1.4735 (isomer mixture, 55% of which being the 3-methyl and 45% of which the 2-methyl derivative)
O-ethyl-O-(1-carbonylmethylazacycloheptane)-sulfite
O-n-propyl-O-(1-carbonylmethylazacycloheptane)-sulfite
O-methyl-O-(1-carbonylmethyl-3-methylazacycloheptane)-sulfite
O-ethyl-O-(1-carbonylmethyl-3-methylazacycloheptane)-sulfite
O-isopropyl-O-(1-carbonylmethyl-3-methylazacycloheptane)-sulfite
O-ethyl-O-(1-carbonylmethyl-4-methylazacycloheptane)-sulfite
O-isopropyl-O-(1-carbonylmethyl-4-methylazacycloheptane)-sulfite
O-methyl-(1-carbonylmethyl-3-azabicyclo-[3,2,0]-heptane)-sulfite
O-ethyl-(1-carbonylmethyl-3-azabicyclo-[3,2,0]-heptane)-sulfite
O-n-propyl-(1-carbonylmethyl-3-azabicyclo-[3,2,0]-heptane)-sulfite
O-isopropyl-(1-carbonylmethyl-3-azabicyclo-[3,2,0]-heptane)-sulfite
O-isopropyl-O-(1-carbonylmethyl-2-methyl-(3-methyl)-azacycloheptane)-sulfite; $n_{25}$ = 1.4698
(isomer mixture, 75% of which is the 2-methyl and 25% of which the 3-methyl derivative)
O-allyl-O-(1-carbonylmethyl-2,3-dimethylazacycloheptane)-sulfite $n_{25}$ = 1.4970
O-allyl-O-(1-carbonylmethylazacycloheptane)-sulfite; $n_{25}$ = 1.5026
O-(butyn-1-yl-3)-O-(1-carbonylmethyl-2,3-dimethylazacycloheptane)-sulfite; $n_{25}$ = 1.4929
O-(butyn-1-yl-3)-O-(1-carbonylmethyl-3-methylazacycloheptane)-sulfite; $n_{25}$ = 1.4965
O-ethyl-O-(1-carbonylmethylazacyclohexane)-sulfite
O-isopropyl-O-(1-carbonylmethylazacyclohexane)-sulfite
O-methyl-O-(1-carbonylmethyl-2-methylazacyclohexane)-sulfite
O-allyl-O-(1-carbonylmethyl-2-methylazacyclohexane)-sulfite
O-isopropyl-O-(1-carbonylmethyl-2-methylazacyclohexane)-sulfite
O-isopropyl-O-(1-carbonylmethyl-3-methylazacyclohexane)-sulfite
O-(β-chloroethyl)-O-(1-carbonylmethyl-3-methylazacyclohexane)-sulfite
O-ethyl-O-(1-carbonylmethyl-4-methylazacyclohexane)-sulfite
O-allyl-O-(1-carbonylmethyl-4-methylazacyclohexane)-sulfite
O-(β-chloroethyl)-O-(1-carbonylmethyl-4-methylazacyclohexane)-sulfite
O-methyl-O-(1-carbonylmethyl-3,3-dimethylazacyclohexane)-sulfite
O-isopropyl-O-(1-carbonylmethyl-3,3-dimethylazacyclohexane)-sulfite
O-(β-chloroethyl)-O-(1-carbonylmethyl-3,5,5-trimethyl)-(3,3,5-trimethylazacycloheptane)-sulfite
(1:1 isomer mixture of the 3,5,5- and the 3,3,5-trimethyl derivative).

A component may make up from 5 to 95 wt%, preferably 20 to 80 wt%, of an active ingredient composition according to the invention.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before of after planting, before sowing, and before, during or after emergence of the crop plant and unwanted plants.

Application may be effected for instance in the form of directly sprayable solutions, powders, suspensions, (including high-percentage oily or aqueous suspensions) dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated caster oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90%, by weight of active ingredient.

There may be added to the compositions or individual active ingredients (if desired, immediately before use (tankmix)) oils of various types, wetting agents or adherents, herbicides, fungicides, nematocides, insecticides, bactericides, trace elements, fertilizers antifoams (e.g., silicones), growth regulators, antidotes and other herbicidally effective compounds such as substituted anilines
    substituted aryloxycarboxylic acids and salts, esters and amides thereof,
    substituted ethers
    substituted arsonic acids and their salts, esters and amides
    substituted benzimidazoles
    substituted benzisothiazoles
    substituted benzothiadiazinone dioxides
    substituted benzoxazines
    substituted benzoxazinones
    substituted benzothiadiazoles
    substituted biurets
    substituted quinolines
    substituted carbamates
    substituted aliphatic carboxylic acids and their salts, esters and amides
    substituted aromatic carboxylic acids and their salts, esters and amides
    substituted carbamoylalkylthiol- or -dithiophosphates
    substituted quinazolines
    substituted cycloalkylamidocarbothiolic acids and their salts, esters and amides
    substituted cycloalkylcarbonamidothiazoles
    substituted dicarboxylic acids and their salts, esters and amides
    substituted dihydrobenzofuranyl sulfonates
    substituted disulfides
    substituted dipyridylium salts
    substituted dithiocarbamates
    substituted dithiophosphoric acids and their salts, esters and amides
    substituted ureas
    substituted hexahydro-1H-carbothioates
    substituted hydantoins
    substituted hydrazides
    substituted hydrazonium salts
    substituted isoxazole pyrimidones
    substituted imidazoles
    substituted isothiazole pyrimidones
    substituted ketones
    substituted naphthoquinones
    substituted aliphatic nitriles
    substituted aromatic nitriles
    substituted oxadiazoles
    substituted oxadiazinones
    substituted oxadiazolidine diones
    substituted oxadiazine diones substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substitutes piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the compositions according to the invention.

These agents may be added to the compositions according to the invention in a ratio by weight of from 1:10 to 10:1. The same applies to oils, fungicides, nematocides, insecticides, bactericides, antidotes and growth regulators.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as

| | |
|---|---|
| *Cynodon spp.* | *Dactylis spp.* |
| *Digitaria spp.* | *Avena spp.* |
| *Echinochloa spp.* | *Bromus spp.* |
| *Setaria spp.* | *Uniola spp.* |
| *Panicum spp.* | *Poa spp.* |
| *Alopecurus spp.* | *Leptochloa spp.* |
| *Lolium spp.* | *Brachiaria spp.* |
| *Sorghum spp.* | *Eleusine spp.* |
| *Agropyron spp.* | *Cenchrus spp.* |
| *Phalaris spp.* | *Eragrostis spp.* |
| *Apera spp.* | *Phragmites communis* |
| etc.; | |
| Cyperaceae, such as | |
| *Carex spp.* | *Eleocharis spp.* |
| *Cyperus spp.* | *Scirpus spp.* |
| etc.; | |
| dicotyledonous weeds, such as | |
| Malvaceae, e.g. | |
| *Abutilon theoprasti* | *Hibiscus spp.* |
| *Sida spp.* | *Malva spp.* |
| etc.; | |
| Compositae, such as | |
| *Ambrosia spp.* | *Centaurea spp.* |
| *Lactuca spp.* | *Tussilago spp.* |
| *Senecio spp.* | *Lapsana communis* |
| *Sonchus spp.* | *Tagetes spp.* |
| *Xanthium spp.* | *Erigeron spp.* |
| *Iva spp.* | *Anthemis spp.* |
| *Galinsoga spp.* | *Matricaria spp.* |
| *Taraxacum spp.* | *Artemisia spp.* |
| *Chrysanthemum spp.* | *Bidens spp.* |
| *Cirsium spp.* | etc.; |
| Convolvulaceae, such as | |
| *Convolvulus spp.* | *Cuscuta spp.* |
| *Ipomoea spp.* | *Jaquemontia tamnifolia* |
| etc.; | |
| Cruciferae, such as | |
| *Barbarea vulgaris* | *Arabidopsis thaliana* |
| *Brassica spp.* | *Descurainia spp.* |
| *Capsella spp.* | *Draba spp.* |
| *Sisymbrium spp.* | *Coronopus didymus* |
| *Thlaspi spp.* | *Lepidium spp.* |
| *Sinapis arvensis* | *Raphanus spp.* |
| etc.; | |
| Geraniaceae, such as | |
| *Erodium spp.* | *Geranium spp.* |
| etc.; | |
| Portulacaceae, such as | |
| *Portulaca spp.* | etc.; |
| Primalaceae, such as | |
| *Anagallis arvensis* | *Lysimachia spp.* |
| etc.; | |
| Rubiaceae, such as | |
| *Richardia spp.* | *Diodia spp.* |
| *Galium spp.* | etc.; |
| Scrophulariacea, such as | |
| *Linaria spp.* | *Digitalis spp.* |
| *Veronica spp.* | etc.; |
| Solanaceae, such as | |
| *Physalis spp.* | *Nicandra spp.* |
| *Solanum spp.* | *Datura spp.* |
| etc.; | |
| Urticaceae, such as | |
| *Urtica spp.* | |
| Violaceae, such as | |
| *Viola spp.* | etc.; |
| Zygophyllaceae, such as | |
| *Tribulus terrestris* | etc.; |
| Euphorbiaceae, such as | |
| *Mercurialis annua* | *Euphorbia spp.* |
| Umbelliferae, such as | |
| *Daucus carota* | *Ammi majus* |
| *Aethusa cynapium* | etc.; |
| Commelinaceae, such as | |
| *Commelina spp.* | etc.; |
| Labiatae, such as | |
| *Lamium spp.* | *Galeopsis spp.* |
| etc.; | |
| Leguminosae, such as | |
| *Medicago spp.* | *Sesbania exaltata* |
| *Trifolium spp.* | *Cassia spp.* |
| *Vicia spp.* | *Lathyrus spp.* |
| etc.; | |
| Plantaginaceae, such as | |
| *Plantago spp.* | etc.; |
| Polygonaceae, such as | |
| *Polygonum spp.* | *Fagopyrum spp.* |
| *Rumex spp.* | etc.; |
| Aizoaceae, such as | |
| *Mollugo verticillata* | etc.; |
| Amaranthaceae, such as | |
| *Amaranthus spp.* | etc.; |
| Boraginaceae, such as | |
| *Amsinckia spp.* | *Anchusa spp.* |

-continued

| | |
|---|---|
| Myostis spp. etc.; | Lithospermum spp. |
| Caryophyllaceae, such as | |
| Stellaria spp. | Silene spp. |
| Spergula spp. | Cerastium spp. |
| Saponaria spp. | Agrostemma githago |
| Scleranthus annuus | etc.; |
| Chenopodiaceae, such as | |
| Chenopodium spp. | Atriplex spp. |
| Kochia spp. | Monolepsis nuttalliana |
| Salsola Kali | etc.; |
| Lythraceae, such as | |
| Cuphea spp. | etc.; |
| Oxalidaceae, such as | |
| Oxalis spp. | |
| Ranunculaceae, such as | |
| Ranunculus spp. | Adonis spp. |
| Delphinium spp. | etc.; |
| Papaveraceae, such as | |
| Papaver spp. etc.; | Fumaria offinicalis |
| Onagraceae, such as | |
| Jussiaea spp. | etc.; |
| Rosaceae, such as | |
| Alchemillia spp. etc.; | Potentilla spp. |
| Potamogetonaceae, such as | |
| Potamogeton spp. | etc.; |
| Najadaceae, such as | |
| Najas spp. | etc.; |
| Equisetaceae | |
| Equisetum spp. | etc.; |
| Marsileaceae, such as | |
| Marsilea quadrifolia | etc.; |
| Polypodiaceae, | |
| Pteridium quilinum | |
| Alismataceae, such as | |
| Alisma spp. etc. | Sagittaria sagittifolia |

The herbicides according to the invention may be employed in cereal crops such as

| | |
|---|---|
| Avena spp. | Sorghum |
| Triticum spp. | Zea mays |
| Hordeum spp. | Panicum miliaceum |
| Secale spp. | Oryza spp. |
| Saccharum offinicarum | | and in dicotyledon crops such as

| | |
|---|---|
| Cruciferae, e.g. | |
| Brassica spp. | Raphanus spp. |
| Sinapis spp. | Lepidium spp. |
| Compositea e.g. | |
| Lactuca spp. | Carthamus spp. |
| Helianthus spp. | Scorzonera spp. |
| malvaceae, e.g. | |
| Gossypium hirsutum | |
| Leguminosae, e.g. | |
| Medicago spp. | Phaseolus spp. |
| Trifolium spp. | Arachis spp. |
| Pisum spp. | Glycine max. |
| Chenopodiaceae, e.g. | |
| Beta vulgaris | |
| Spinacia spp. | |
| Solanaceae, e.g. | |
| Solanum spp. | Capsicum annuum |
| Nicotiania spp. | |
| Linaceae, e.g. | |
| Linum spp. | |
| Umbelliferae, e.g. | |
| Petroselinum spp. | Apiam graveolens |
| Daucus carota | |
| Rosaceae e.g. | Fragaria |
| Cucurbitaceae, e.g. | |
| Cucumis spp. | Cucurbita spp. |
| Liliaceae e.g. | |
| Allium spp. | |
| Vitaceae, e.g. | |
| Vitis vinifera | |
| Bromeliaceae, e.g. | |
| Ananas sativus. | |

The compositions may also be used as total agents on ditches, aquatic areas, railway track, waste and barren land, etc.

The compositions according to the invention were tested in the greenhouse and in the open. Their action corresponds to that of the compositions employed in the following examples.

EXAMPLE 1

An agricultural plot was sown with various seeds. The soil was then immediately treated with the following amounts of the following individual active ingredients and compositions thereof as dispersions, emulsions or granules:

I 1-phenyl-4-amino-5-chloropyridazone-(6)
III O-(methylaminosulfonyl)-glycolic acid-N-isopropylanilide
IV 2,3-dichloroallyl N,N-diisopropylthiolcarbamate
V 2,3,3-trichloroallyl N,N-diisopropylthiolcarbamate
VI 2-ethoxy-2,3-dihydro-3,3-dimethyl-5-benzofuranylmethane sulfonate
VIII 2,3-dihydro-3,3-dimethyl-2-ethoxybenzofuran-5-yldimethylamino sulfonate
IX ethyl N-ethyl-N-cyclohexylthiocarbamate, each at rates of 0.5, 1 and 2 kg/ha;

I+III+IV, I+III+V, I+III+VI, I+III+VIII and I+III+IX, each at rates of 1+0.5+0.5, 0.5+1+0.5 and 0.5+0.5+1 kg/ha.

After 4 to 5 weeks it was ascertained that the compositions had a better herbicidal action than their components, combined with the same crop tolerance.

The results are given below:

| Active ingredient kg/ha | I 0.5 | 1 | 2 | III 0.5 | 1 | 2 | IV 0.5 | 1 | 2 |
|---|---|---|---|---|---|---|---|---|---|
| Crop plants: | | | | | | | | | |
| Beta vulgaris | 0 | 0 | 0 | 0 | 0 | 0 | 0 | 0 | 10 |
| Unwanted plants: | | | | | | | | | |
| Avena fatua | 5 | 12 | 20 | 15 | 40 | 54 | 20 | 50 | 95 |
| Echinochloa crus-galli | 6 | 13 | 32 | 25 | 70 | 100 | 10 | 20 | 50 |
| Matricaria chamomilla | 20 | 40 | 85 | 15 | 35 | 80 | 5 | 10 | 19 |

| Active ingredient kg/ha | V 0.5 | 1 | 2 | VI 0.5 | 1 | 2 | VIII 0.5 | 1 | 2 | IX 0.5 | 1 | 2 |
|---|---|---|---|---|---|---|---|---|---|---|---|---|
| Beta vulgaris | 0 | 0 | 0 | 2.5 | 4 | 10 | 0 | 0 | 0 | 0 | 0 | 0 |
| Avena fatua | 25 | 50 | 95 | 16 | 40 | 80 | 45 | 80 | 100 | 10 | 30 | 60 |
| Echinochloa crus-galli | 10 | 20 | 50 | 20 | 30 | 70 | 70 | 90 | 100 | 20 | 30 | 80 |
| Matricaria chamomilla | 9 | 12 | 21 | 20 | 40 | 70 | 5 | 20 | 50 | 5 | 7 | 10 |

| Active ingredient kg/ha | I + III + IV 1+ 0.5+ 0.5 | 0.5+ 1+ 0.5 | 0.5+ 0.5+ 1 | I + III + V 1+ 0.5+ 0.05+ | 0.5+ 1+ 0.5 | 0.5+ 0.5+ 1 | I + III + VI 1+ 0.5+ 0.5+ | 0.5+ 1+ 0.5 | 0.5+ 0.5+ 1 |
|---|---|---|---|---|---|---|---|---|---|
| Crop plants: | | | | | | | | | |
| Beta vulgaris | 0 | 0 | 0 | 0 | 0 | 0 | 2.5 | 2.5 | 4 |
| Unwanted plants: | | | | | | | | | |
| Avena fatua | 85 | 95 | 100 | 90 | 100 | 100 | 85 | 90 | 95 |
| Echinochloa crus-galli | 91 | 100 | 100 | 98 | 100 | 100 | 100 | 100 | 100 |

| Matricaria chamomilla | 90 | 97 | 85 | 95 | 95 | 90 | 100 | 100 | 100 |
| Active ingredient | I + III + VIII | | | I + III + IX | | | | | |
| Beta vulgaris | 0 | 0 | 0 | 0 | 0 | 0 | | | |
| Avena fatua | 100 | 100 | 100 | 80 | 90 | 85 | | | |
| Echinochloa crus-galli | 100 | 100 | 100 | 96 | 100 | 100 | | | |
| Matricaria chamomilla | 90 | 90 | 95 | 100 | 97 | 90 | | | |

0 = no damage
100 = complete destruction

EXAMPLE 2

An agricultural plot was sown with various seeds. The soil was then immediately treated with the following amounts of the following individual active ingredients and compositions thereof as dispersions or emulsions:

I 1-phenyl-4-amino-5-chloropyridazone-(6)
III O-(methylaminosulfonyl)-glycolic acid-N-isopropylanilide
IV 2,3-dichloroallyl N,N-diisopropylthiolcarbamate
V 2,3,3-trichloroallyl N,N-diisopropylthiolcarbamate
VI 2-ethoxy-2,3-dihydro-3,3-dimethyl-5-benzofuranylmethane sulfonate
VIII 2,3-dihydro-3,3-dimethyl-2-ethoxybenzofuran-5-yldimethylamino sulfonate
IX ethyl N-ethyl-N-cyclohexylthiolcarbamate, each at rates of 1, 1.5, 2, 3, 4, 4.5, 5 and 6 kg/ha;

I+III+IV, I V, I+III+VI, I+III+VIII and I+III+IX, each at rates of 1+1+1, 2+1+1, 1+2+1, 1+1+2, 1.5+1.5+1.5, 3+1+1, 1+3+1, 1+1+3 and 2+2+2 kg/ha; and for comparison
X N-(4-chlorophenyl)-N',N'-dimethylurea, 3 and 5 kg/ha; I+II+X 1+1+3 kg/ha.

After 4 to 5 weeks it was ascertained that the compositions I+III+IV, I+III+V, I+III+VI, I+III+ VIII and I+III+IX had better crop tolerence than the composition I+II+X, combined with the same weed control.

The results are given below:

| Active ingredient kg/ha | 1 | 1.5 | 2 | I 3 | 4 | 4.5 | 5 | 6 |
|---|---|---|---|---|---|---|---|---|
| Crop plants: | | | | | | | | |
| Beta vulgaris | 0 | 0 | 0 | 0 | 10 | 13 | 15 | 20 |
| Unwanted plants: | | | | | | | | |
| Avena fatua | 12 | 15 | 20 | 40 | 75 | 85 | 90 | 100 |
| Echinochloa crus-galli | 13 | 20 | 32 | 65 | 75 | 80 | 90 | 100 |
| Matricaria chamomilla | 40 | 60 | 85 | 100 | 100 | 100 | 100 | 100 |
| Active ingredient | | | | III | | | | |
| Beta vulgaris | 0 | 0 | 0 | 0 | 10 | 15 | 20 | 30 |
| Avena fatua | 40 | 45 | 54 | 75 | 80 | 65 | 90 | 85 |
| Echinochloa crus-galli | 70 | 90 | 100 | 100 | 100 | 100 | 100 | 100 |
| Matricaria chamomilla | 35 | 65 | 80 | 90 | 95 | 100 | 100 | 100 |
| Active ingredient kg/ha | 1 | 1.5 | 2 | IV 3 | 4 | 4.5 | 5 | 6 |
| Beta vulgaris | 0 | 0 | 10 | 15 | 25 | 30 | 35 | 45 |
| Avena fatua | 50 | 83 | 95 | 100 | 100 | 100 | 100 | 100 |
| Echinochloa crus-galli | 20 | 40 | 50 | 80 | 90 | 100 | 100 | 100 |
| Matricaria chamomilla | 10 | 13 | 19 | 30 | 40 | 45 | 55 | 70 |
| Active ingredient | | | | V | | | | |
| Beta vulgaris | 0 | 0 | 7 | 10 | 20 | 28 | 35 | 40 |
| Avena fatua | 50 | 90 | 95 | 100 | 100 | 100 | 100 | 100 |
| Echinochloa crus-galli | 20 | 50 | 50 | 90 | 96 | 100 | 100 | 100 |
| Matricaria chamomilla | 12 | 15 | 21 | 32 | 45 | 50 | 60 | 75 |
| Active ingredient | | | | VI | | | | |
| Beta vulgaris | 4 | 5 | 10 | 20 | 25 | 30 | 35 | 40 |
| Avena fatua | 40 | 60 | 80 | 100 | 100 | 100 | 100 | 100 |
| Echinochloa crus-galli | 30 | 70 | 70 | 100 | 100 | 100 | 100 | 100 |
| Matricaria chamomilla | 40 | 50 | 70 | 80 | 95 | 100 | 100 | 100 |
| Active ingredient | | | | VIII | | | | |
| Beta vulgaris | 0 | 0 | 0 | 5 | 10 | 12 | 18 | 25 |
| Avena fatua | 80 | 100 | 100 | 100 | 100 | 100 | 100 | 100 |
| Echinochloa crus-galli | 90 | 100 | 100 | 100 | 100 | 100 | 100 | 100 |
| Matricaria chamomilla | 20 | 30 | 50 | 70 | 92 | 100 | 100 | 100 |
| Active ingredient | | | | IX | | | | |
| Beta vulgaris | 0 | 0 | 0 | 0 | 10 | 12 | 15 | 20 |
| Avena fatua | 30 | 40 | 60 | 95 | 100 | 100 | 100 | 100 |
| Echinochloa crus-galli | 30 | 60 | 80 | 95 | 100 | 100 | 100 | 100 |
| Matricaria chamomilla | 7 | 9 | 10 | 16 | 48 | 55 | 60 | 75 |
| | I + III + IV | | | | | | | |
| Active ingredient kg/ha | 1+ 1+ 1 | 2+ 1+ 1 | 1+ 2+ 1 | 1+ 1+ 2 | 1.5+ 1.5+ 1.5 | 3+ 1+ 1 | 1+ 3+ 1 | 2+ 2+ 2 |
| Beta vulgaris | 0 | 0 | 0 | 10 | 0 | 0 | 15 | 10 |
| Avena fatua | 100 | 100 | 100 | 100 | 100 | 100 | 100 | 100 |
| Echinochloa crus-galli | 100 | 100 | 100 | 100 | 100 | 100 | 100 | 100 |
| Matricaria chamomilla | 100 | 100 | 100 | 100 | 100 | 100 | 100 | 100 |
| Active ingredient | I + III + V | | | | | | | |
| Beta vulgaris | 0 | 0 | 0 | 7 | 0 | 0 | 10 | 7 |
| Avena fatua | 100 | 100 | 100 | 100 | 100 | 100 | 100 | 100 |
| Echinochloa crus-galli | 100 | 100 | 100 | 100 | 100 | 100 | 100 | 100 |

-continued

| | | | | | | | | | |
|---|---|---|---|---|---|---|---|---|---|
| Matricaria chamomilla | 100 | 100 | 100 | 100 | 100 | 100 | 100 | 100 | 100 |
| Active ingredient | I + III + VI | | | | | | | | |
| Beta vulgaris | 4 | 4 | 4 | 10 | 5 | 4 | 4 | 20 | 10 |
| Avena fatua | 100 | 100 | 100 | 100 | 100 | 100 | 100 | 100 | 100 |
| Echinochloa crus-galli | 100 | 100 | 100 | 100 | 100 | 100 | 100 | 100 | 100 |
| Matricaria chamomilla | 100 | 100 | 100 | 100 | 100 | 100 | 100 | 100 | 100 |
| Active ingredient | I + III + VIII | | | | | | | | |
| Beta vulgaris | 0 | 0 | 0 | 0 | 0 | 0 | 0 | 5 | 0 |
| Avena fatua | 100 | 100 | 100 | 100 | 100 | 100 | 100 | 100 | 100 |
| Echinochloa crus-galli | 100 | 100 | 100 | 100 | 100 | 100 | 100 | 100 | 100 |
| Matricaria chamomilla | 100 | 100 | 100 | 100 | 100 | 100 | 100 | 100 | 100 |
| Active ingredient | I + III + IX | | | | | | | | |
| Beta vulgaris | 0 | 0 | 0 | 0 | 0 | 0 | 0 | 0 | 0 |
| Avena fatua | 100 | 100 | 100 | 100 | 100 | 100 | 100 | 100 | 100 |
| Echinochloa crus-galli | 100 | 100 | 100 | 100 | 100 | 100 | 100 | 100 | 100 |
| Matricaria chamomilla | 100 | 100 | 100 | 100 | 100 | 100 | 100 | 100 | 100 |
| Active ingredient kg/ha | | | X 3 | | | 5 | | I+II+X | 1+1+3 |
| Beta vulgaris | | | 100 | | | 100 | | | 100 |
| Avena fatua | | | 100 | | | 100 | | | 100 |
| Echinochloa crus-galli | | | 100 | | | 100 | | | 100 |
| Matricaria chamomilla | | | 100 | | | 100 | | | 100 |

0 = no damage
100 = complete destruction

EXAMPLE 3

In the greenhouse, loamy sandy soil was filled into pots and sown with various seeds. The soil prepared in this manner was then treated with the following amounts of the following individual active ingredients and compositions thereof as granules:

I 1-phenyl-4-amino-5-chloropyridazone-(6)
II O-(isopropylaminosulfonyl)-glycolic acid-N-butyn-1-yl-3-anilide
III O-(methylaminosulfonyl)-glycolic acid-N-isopropylanilide,
XXXXII ethyl N,N-di-n-propylthiolcarbamate
XXXXIII n-propyl N-ethyl-N-butylthiolcarbamate
each at rates of 0.5, 1, 1.5 and 2 kg/ha;

I+II+XXXII, I+II+XXXXIII, I+III+XXXXII and I+III+XXXXIII, each at rates of 0.5+0.5+0.5, 1+0.5+0.5, 0.5+1+0.5 and 0.5+0.5+1 kg/ha;

II+XXXXII, II+XXXXIII, III+XXXXII and III+XXXXIII, each at rates of 0.5+0.5, 1+0.5, 0.5+1 and 1+1 kg/ha.

After 4 to 5 weeks it was ascertained that, at the low application rates, the compositions had a better weed control than their components, combined with the same crop tolerance. At the higher application rates, the crop tolerance was still good.

The results are given below:

| Active ingredient kg/ha | I | | | | II | | | | III | | | |
|---|---|---|---|---|---|---|---|---|---|---|---|---|
| | 0.5 | 1 | 1.5 | 2 | 0.5 | 1 | 1.5 | 2 | 0.5 | 1 | 1.5 | 2 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 5 | 12 | 15 | 20 | 40 | 60 | 65 | 75 | 15 | 40 | 45 | 54 |
| Echinochloa crus-galli | 6 | 13 | 20 | 32 | 60 | 70 | 95 | 100 | 60 | 70 | 90 | 100 |
| Matricaria chamomilla | 20 | 40 | 60 | 85 | 15 | 40 | 60 | 80 | 15 | 35 | 55 | 80 |
| Active ingredient | XXXXII | | | | XXXXIII | | | | | | | |
| Beta vulgaris | 0 | 0 | 0 | 0 | 0 | 0 | 0 | 0 | | | | |
| Avena fatua | 20 | 27 | 40 | 54 | 20 | 30 | 45 | 59 | | | | |
| Echinochloa crus-galli | 28 | 45 | 60 | 80 | 24 | 41 | 55 | 75 | | | | |
| Matricaria chamomilla | 10 | 26 | 40 | 50 | 20 | 20 | 25 | 35 | | | | |
| Active ingredient kg/ha | I + II + XXXXII | | | | I + II + XXXXIII | | | | I + III + XXXXII | | | |
| | 0.5+ 0.5+ 0.5 | 1+ 0.5+ 0.5 | 0.5+ 1+ 0.5 | 0.5+ 0.5+ 1 | 0.5+ 0.5+ 0.5 | 1+ 0.5+ 0.5 | 0.5+ 1+ 0.5 | 0.5+ 0.5+ 1 | 0.5+ 0.5+ 0.5 | 1+ 0.5+ 0.5 | 0.5+ 1+ 0.5 | 0.5+ 0.5+ 1 |
| Beta vulgaris | 0 | 0 | 0 | 0 | 0 | 0 | 0 | 0 | 0 | 0 | 0 | 0 |
| Avena fatua | 100 | 100 | 100 | 100 | 100 | 100 | 100 | 100 | 80 | 89 | 100 | 87 |
| Echinochloa crus-galli | 100 | 100 | 100 | 100 | 100 | 100 | 100 | 100 | 100 | 100 | 100 | 100 |
| Matricaria chamomilla | 85 | 100 | 100 | 100 | 95 | 100 | 100 | 100 | 86 | 100 | 100 | 100 |
| Active ingredient | I + III + XXXXIII | | | | | | | | | | | |
| Beta vulgaris | 0 | 0 | 0 | 0 | | | | | | | | |
| Avena fatua | 80 | 88 | 100 | 92 | | | | | | | | |
| Echinochloa crus-galli | 100 | 100 | 100 | 100 | | | | | | | | |
| Matricaria chamomilla | 95 | 100 | 100 | 95 | | | | | | | | |
| Active ingredient kg/ha | II + XXXXII | | | | II + XXXXIII | | | | | | | |
| | 0.5+ 0.5 | 1+ 0.5 | 0.5+ 1 | 1+1 | 0.5+ 0.5 | 1+ 0.5 | 0.5+ 1 | 1+1 | | | | |
| Beta vulgaris | 0 | 0 | 0 | 0 | 0 | 0 | 0 | 0 | | | | |
| Avena fatua | 97 | 100 | 100 | 100 | 98 | 100 | 100 | 100 | | | | |
| Echinochloa crus-galli | 100 | 100 | 100 | 100 | 100 | 100 | 100 | 100 | | | | |
| Matricaria chamomilla | 65 | 90 | 82 | 100 | 75 | 100 | 76 | 100 | | | | |
| Active ingredient | III + XXXXII | | | | III + XXXXIII | | | | | | | |
| Beta vulgaris | 0 | 0 | 0 | 0 | 0 | 0 | 0 | 0 | | | | |
| Avena fatua | 75 | 100 | 85 | 100 | 76 | 97 | 85 | 100 | | | | |

| | | | | | | | | |
|---|---|---|---|---|---|---|---|---|
| Echinochloa crus-galli | 100 | 100 | 100 | 100 | 100 | 100 | 100 | 100 |
| Matricaria chamomilla | 67 | 85 | 82 | 100 | 75 | 95 | 75 | 97 |

0 = no damage
100 = complete destruction

EXAMPLE 4

In the greenhouse, loamy sandy soil was filled into pots and sown with various seeds. The soil prepared in this manner was then treated with the following amounts of the following individual active ingredients and compositions thereof as emulsions or dispersions:

I 1-phenyl-4-amino-5-chloropyridazone-(6) 0.5, 1, 1.5, 1.86, 2.5, 3, 4 and 5 kg/ha, III O-(methylaminosulfonyl)-glycolic acid-N-isopropylanilide, 0.5, 0.75, 1, 1.25, 1.33, 1.5, 1.66, 2, 3, 4 and 5 kg/ha, IV 2,3-dichloroallyl N,N-diisopropylthiolcarbamate 0.25, 0.5, 0.75, 1, 1.5, 2 and 4 kg/ha, XXIV O-(methylaminosulfonyl)-glycolic acid hexamethylene amide, 0.25, 0.375, 0.5, 0.67, 0.725, 0.75, 0.834, 1, 1.5, 2, 2.5, 3, 3.5, 4 and 5 kg/ha, I+XXIV+III  1+0.5+0.5, 1.5+0.75+0.75, 2+1+1, 2+0.5+1.5, 1.86+0.375+0.75, 2.5+0.5+1, 3+0.725+1.25, 3+0.5+1.5, 2+0.67+1.33, 2.5+0.834+1.66 and 2+1+2 kg/ha, I+XXIV+IV  2+1+1, 2+1.5+0.5, 2+0.5+1.5, 1+0.5+0.5, 1+0.75+0.25, and 1+0.25+0.75 kg/ha.

After 4 to 5 weeks it was ascertained that the compositions had a better herbicidal action than their components, combined with superior crop plant compatibility. The results are given below:

| kg/ha | 0.5 | 1 | 1.5 | 1.86 | 2 | 2.5 | 3 | 4 | 5 |
|---|---|---|---|---|---|---|---|---|---|
| Crop plants: | | | | | | | | | |
| Beta vulgaris | 0 | 0 | 0 | 0 | 0 | 0 | 0 | 10 | 15 |
| Unwanted plants: | | | | | | | | | |
| Avena fatua | 5 | 12 | 15 | 18 | 20 | 25 | 40 | 75 | 90 |
| Echinochloa crus-galli | 6 | 13 | 20 | 27 | 32 | 50 | 65 | 75 | 90 |
| Stellaria media | 20 | 45 | 60 | 70 | 80 | 90 | 95 | 100 | 100 |
| Galium aparine | 15 | 40 | 50 | 68 | 75 | 80 | 85 | 90 | 95 |
| Chenopodium album | 25 | 40 | 60 | 73 | 80 | 90 | 95 | 100 | 100 |
| Alopecurus myosuroides | 6 | 11 | 19 | 20 | 22 | 25 | 30 | 45 | 60 |
| Lamium amplexicaule | 10 | 20 | 25 | 33 | 40 | 60 | 70 | 90 | 100 |

| Active ingredient III kg/ha | 0.5 | 0.75 | 1 | 1.25 | 1.33 | 1.5 | 1.66 | 2 | 3 | 4 | 5 |
|---|---|---|---|---|---|---|---|---|---|---|---|
| Beta vulgaris | 0 | 0 | 0 | 0 | 0 | 0 | 0 | 0 | 0 | 10 | 20 |
| Avena fatua | 15 | 30 | 40 | 43 | 45 | 45 | 47 | 54 | 75 | 80 | 90 |
| Echinochloa crus-galli | 25 | 45 | 70 | 80 | 86 | 90 | 93 | 100 | 100 | 100 | 100 |
| Stellaria media | 10 | 20 | 25 | 30 | 38 | 45 | 48 | 55 | 65 | 70 | 85 |
| Galium aparine | 10 | 12 | 15 | 18 | 22 | 25 | 26 | 30 | 40 | 43 | 45 |
| Chenopodium album | 15 | 17 | 20 | 25 | 30 | 35 | 38 | 45 | 50 | 57 | 65 |
| Alopecurus myosuroides | 20 | 40 | 50 | 60 | 75 | 90 | 94 | 100 | 100 | 100 | 100 |
| Lamium amplexicaule | 10 | 15 | 20 | 25 | 27 | 35 | 40 | 55 | 60 | 70 | 75 |

| Active ingredient IV kg/ha | 0.25 | 0.5 | 0.75 | 1 | 1.5 | 2 | 4 |
|---|---|---|---|---|---|---|---|
| Beta vulgaris | 0 | 0 | 0 | 0 | 0 | 10 | 25 |
| Avena fatua | 10 | 20 | 30 | 50 | 83 | 95 | 100 |
| Echinochloa crus-galli | 0 | 10 | 15 | 20 | 40 | 50 | 90 |
| Stellaria media | 6 | 7 | 10 | 13 | 15 | 18 | 25 |
| Galium aparine | 0 | 0 | 0 | 0 | 5 | 8 | 15 |
| Chenopodium album | 0 | 5 | 7 | 10 | 15 | 20 | 33 |
| Alopecurus myosuroides | 11 | 26 | 35 | 58 | 85 | 95 | 100 |
| Lamium amplexicaule | 0 | 5 | 9 | 12 | 15 | 20 | 25 |

| Active ingredient XXIV kg/ha | 0.25 | 0.375 | 0.5 | 0.67 | 0.725 | 0.75 | 0.834 | 1 | 1.5 | 2 | 2.5 |
|---|---|---|---|---|---|---|---|---|---|---|---|
| Beta vulgaris | 0 | 0 | 0 | 0 | 0 | 0 | 0 | 0 | 0 | 0 | 0 |
| Avena fatua | 15 | 20 | 25 | 27 | 30 | 35 | 45 | 60 | 75 | 80 | 85 |
| Echinochloa crus-galli | 20 | 31 | 35 | 39 | 42 | 45 | 55 | 60 | 90 | 100 | 100 |
| Stellaria media | 20 | 23 | 25 | 27 | 28 | 30 | 40 | 50 | 75 | 85 | 90 |
| Galium aparaine | 15 | 18 | 25 | 25 | 28 | 30 | 33 | 40 | 50 | 65 | 70 |
| Chenopodium album | 15 | 20 | 30 | 31 | 33 | 35 | 37 | 40 | 45 | 60 | 65 |
| Alopecurus myosuroides | 25 | 30 | 40 | 45 | 49 | 60 | 65 | 75 | 90 | 95 | 100 |
| Lamium amplexicaule | 20 | 23 | 25 | 27 | 30 | 30 | 40 | 50 | 70 | 80 | 90 |

| Active ingredient XXIV kg/ha | 3 | 3.5 | 4 | 5 |
|---|---|---|---|---|
| Beta vulgaris | 5 | 7 | 10 | 18 |
| Avena fatua | 90 | 96 | 100 | 100 |
| Echinochloa crus-galli | 100 | 100 | 100 | 100 |
| Stellaria media | 95 | 100 | 100 | 100 |
| Galium aparine | 75 | 80 | 85 | 95 |
| Chenopodium album | 70 | 80 | 90 | 100 |
| Alopecurus myosuroides | 100 | 100 | 100 | 100 |
| Lamium amplexicaule | 95 | 100 | 100 | 100 |

| Active ingredient I + XXIV + III kg/ha | 1+ 0.5+ 0.5 | 1.5+ 0.75+ 0.75 | 2+ 1+ 1 | 2+ 0.5+ 1.5 | 1.86+ 0.375 +0.75 | 2.5+ 0.5+ 1 | 3+ 0.725+ 1.25 | 3+ 0.5+ 1.5 |
|---|---|---|---|---|---|---|---|---|
| Beta vulgaris | 0 | 0 | 0 | 0 | 0 | 0 | 0 | 0 |
| Avena fatua | 92 | 100 | 100 | 100 | 100 | 100 | 100 | 100 |
| Echinochloa crus-galli | 100 | 100 | 100 | 100 | 100 | 100 | 100 | 100 |
| Stellaria media | 100 | 100 | 100 | 100 | 100 | 100 | 100 | 100 |
| Galium aparine | 100 | 100 | 100 | 100 | 100 | 100 | 100 | 100 |

| | I + XXIV + III | | | | I + XXIV + IV | | | |
|---|---|---|---|---|---|---|---|---|
| | 2+ 0.67+ 1.33 | 2.5+ 0.834+ 1.66 | 2+1 +2 | 2+1+1 | 2+ 1.5+ 0.5 | 2+ 0.5+ 1.5 | 1+ 0.5+ 0.5 | 1+ 0.73+ 0.25 | 1+ 0.25+ 0.75 |
| Chenopodium album | 100 | 100 | 100 | 100 | 100 | 100 | 100 | 100 | |
| Lamium amplexicaule | 95 | 100 | 100 | 100 | 100 | 100 | 100 | 100 | |
| Beta vulgaris | 0 | 0 | 0 | 0 | 0 | 0 | 0 | 0 | 0 |
| Avena fatua | 100 | 100 | 100 | 100 | 100 | 100 | 97 | 100 | 100 |
| Echinochloa crus-galli | 100 | 100 | 100 | 100 | 100 | 100 | 100 | 100 | 100 |
| Stellaria media | 100 | 100 | 100 | 100 | 100 | 100 | 100 | 100 | 100 |
| Galium aparine | 100 | 100 | 100 | 100 | 100 | 100 | 100 | 100 | 95 |
| Chenopodium album | 100 | 100 | 100 | 100 | 100 | 100 | 100 | 100 | 90 |
| Alopecurus myosuroides | 100 | 100 | 100 | 100 | 100 | 100 | 100 | 100 | 100 |
| Lamium amplexicaule | 100 | 100 | 100 | 100 | 100 | 100 | 95 | 90 | 75 |

EXAMPLE 5

In the greenhouse, loamy sandy soil was filled into pots and sown with various seeds. The soil prepared in this manner was then treated with the following amounts of the following individual active ingredients and compositions thereof as dispersions or emulsions:

I 1-phenyl-4-amino-5-chloropyridazone-(6) 0.5, 1, 1.5, 2, 2.5, 3, 4, 5 and 6 kg/ha, III O-(methylaminosulfonyl)-glycolic acid-N-isopropylanilide 0.25, 0.5, 0.75, 1, 1.5, 2, 2.5, 3, 4, 5 and 6 kg/ha, IV 2,3-dichloroallyl N,N-diisopropylthiolcarbamate 0.25, 0.5, 0.75, 1, 1.5, 2 and 4 kg/ha, XXXXVI 2,3-dihydro-3,3-dimethyl-2-ethoxybenzofuran-5-yl-N-methyl-N-acetylaminosulfonate 0.25, 0.5, 0.75, 1, 1.5, 2, 3, 4 and 6 kg/ha, I+III+IV 2+1+1, 2+1.5+0.5, 2+0.5+1.5, 1+0.5+0.5, 1+0.75+0.25, and 1+0.25+0.75 kg/ha, I+III+XXXXVI 1.5+0.75+0.75, 2+1+1, 0.5+0.25+0.25, 1+0.5+0.5, 2+1.5+0.5, 2+0.5+1.5, 3+1.5+1.5, 3+1+2 and 3+2+1 kg/ha.

After 4 to 5 weeks it was ascertained that the compositions had a better herbicidal action than their components, combined with superior crop plant compatibility.

The results are given below:

| Active ingredient kg/ha | I | | | | | | | | |
|---|---|---|---|---|---|---|---|---|---|
| | 0.5 | 1 | 1.5 | 2 | 2.5 | 3 | 4 | 5 | 6 |
| Crop plants: | | | | | | | | | |
| Beta vulgaris | 0 | 0 | 0 | 0 | 0 | 0 | 10 | 15 | 20 |
| Unwanted plants: | | | | | | | | | |
| Avena fatua | 5 | 12 | 15 | 20 | 25 | 40 | 75 | 90 | 100 |
| Echinochloa crus-galli | 6 | 13 | 20 | 32 | 50 | 65 | 75 | 90 | 100 |
| Stellaria media | 20 | 45 | 60 | 80 | 90 | 95 | 100 | 100 | 100 |
| Galium aparine | 15 | 40 | 50 | 75 | 80 | 85 | 90 | 95 | 100 |
| Chenopodium album | 25 | 40 | 60 | 80 | 90 | 95 | 100 | 100 | 100 |
| Alopecurus myosuroides | 6 | 11 | 19 | 22 | 25 | 30 | 45 | 60 | 95 |
| Lamium amplexicaule | 10 | 20 | 25 | 40 | 60 | 70 | 90 | 100 | 100 |
| Active ingredient kg/ha | III | | | | | | | | |
| | 0.25 | 0.5 | 0.75 | 1 | 1.5 | 2 | 2.5 | 3 | 4 | 5 | 6 |
| Beta vulgaris | 0 | 0 | 0 | 0 | 0 | 0 | 0 | 0 | 10 | 20 | 30 |
| Avena fatua | 10 | 15 | 30 | 40 | 45 | 54 | 70 | 75 | 80 | 90 | 85 |
| Echinochloa crus-galli | 20 | 25 | 45 | 70 | 90 | 100 | 100 | 100 | 100 | 100 | 100 |
| Stellaria media | 5 | 10 | 20 | 25 | 45 | 55 | 60 | 65 | 70 | 85 | 100 |
| Galium aparine | 5 | 10 | 12 | 15 | 25 | 30 | 35 | 40 | 43 | 45 | 60 |
| Chenopodium album | 10 | 15 | 17 | 20 | 35 | 45 | 60 | 50 | 57 | 65 | 75 |
| Alopocurus myosuroides | 10 | 20 | 40 | 50 | 90 | 100 | 100 | 100 | 100 | 100 | 100 |
| Lamium amplexicaule | 7 | 10 | 15 | 20 | 35 | 55 | 70 | 60 | 70 | 75 | 90 |
| Active ingredient kg/ha | IV | | | | | | |
| | 0.25 | 0.5 | 0.75 | 1 | 1.5 | 2 | 4 |
| Beta vulgaris | 0 | 0 | 0 | 0 | 0 | 10 | 25 |
| Avena fatua | 10 | 20 | 30 | 50 | 85 | 95 | 100 |
| Echinochloa crus-galli | 0 | 10 | 15 | 20 | 40 | 50 | 90 |
| Stellaria media | 6 | 7 | 10 | 13 | 15 | 18 | 25 |
| Galium aparine | 0 | 0 | 0 | 0 | 5 | 8 | 15 |
| Chenopodium album | 0 | 5 | 7 | 10 | 15 | 20 | 35 |
| Alopecurus myosuroides | 11 | 26 | 35 | 58 | 85 | 95 | 100 |
| Lamium amplexicaule | 0 | 5 | 9 | 12 | 15 | 20 | 25 |
| Active ingredient kg/ha | VIII | | | | | | |
| | 0.25 | 0.5 | 0.75 | 1 | 1.5 | 2 | 3 | 4 |
| Beta vulgaris | 0 | 0 | 0 | 0 | 0 | 0 | 5 | 10 |
| Avena fatua | 30 | 45 | 65 | 80 | 100 | 100 | 100 | 100 |
| Echinochloa crus-galli | 50 | 70 | 80 | 90 | 100 | 100 | 100 | 100 |
| Stellaria media | 50 | 60 | 65 | 75 | 95 | 100 | 100 | 100 |
| Galium aparine | 10 | 20 | 30 | 40 | 52 | 70 | 80 | 95 |
| Chenopodium album | 20 | 30 | 37 | 45 | 65 | 75 | 85 | 95 |
| Alopecurus myosuroides | 35 | 50 | 65 | 75 | 96 | 100 | 100 | 100 |
| Lamium amplexicaule | 15 | 25 | 50 | 70 | 80 | 90 | 100 | 100 |
| Active ingredient kg/ha | I + III + IV | | | | | |
| | 2+1+1 | 2+ 1.5+ 0.5 | 2+ 0.5+ 1.5 | 1+ 0.5+ 0.5 | 1+ 0.75+ 0.25 | 1+ 0.25+ 0.75 |
| Crop plants: | | | | | | |
| Beta vulgaris | 0 | 0 | 0 | 0 | 0 | 0 |
| Unwanted plants: | | | | | | |
| Avena fatua | 100 | 100 | 100 | 90 | 85 | 95 |
| Echinochloa crus-galli | 100 | 100 | 100 | 90 | 100 | 90 |

| | | | | | | |
|---|---|---|---|---|---|---|
| *Stellaria media* | 100 | 100 | 100 | 100 | 100 | 100 |
| *Galium aparine* | 100 | 100 | 100 | 90 | 95 | 85 |
| *Chenopodium album* | 100 | 100 | 100 | 85 | 85 | 83 |
| *Alopecurus myosuroides* | 100 | 100 | 100 | 100 | 100 | 100 |
| *Lamium amplexicaule* | 100 | 100 | 100 | 75 | 75 | 78 |

| Active ingredient kg/ha | 1.5+0.75+0.75 | 2+1+1 | I + III + XXXVI | | | | | 3+1+2 | 3+2+1 |
|---|---|---|---|---|---|---|---|---|---|
| | | | 0.5+0.25+0.25 | 1+0.5+0.5 | 2+1.5+0.5 | 2+0.5+1.5 | 3+1.5+1.5 | | |
| *Beta vulgaris* | 0 | 0 | 0 | 0 | 0 | 0 | 0 | 0 | 0 |
| *Avena fatua* | 100 | 100 | 75 | 97 | 100 | 100 | 100 | 100 | 100 |
| *Echinochloa crus-galli* | 100 | 100 | 86 | 100 | 100 | 100 | 100 | 100 | 100 |
| *Stellaria media* | 100 | 100 | 80 | 100 | 100 | 100 | 100 | 100 | 100 |
| *Galium aparine* | 100 | 100 | 75 | 100 | 100 | 100 | 100 | 100 | 100 |
| *Chenopodium album* | 100 | 100 | 65 | 90 | 100 | 100 | 100 | 100 | 100 |
| *Alopecurus myosuroides* | 100 | 100 | 75 | 100 | 100 | 100 | 100 | 100 | 100 |
| *Lamium amplexicaule* | 100 | 100 | 75 | 100 | 100 | 100 | 100 | 100 | 100 |

0 = no damage
100 + complete destruction

I claim:

1. A herbicide composition comprising an inert carrier having dispersed therein a herbicidally effective amount of a mixture consisting essentially of 20–80 wt % of each of:
   a. O-(methylaminosulfonyl)-glycolic acid-N-isopropylanilide O-(isopropylaminosulfonyl)-glycolic acid N-butyn-1-yl-3-anilide, or O-(methylaminosulfonyl)-glycolic acid hexamethylene amide,
   b. 1-phenyl-4-amino-5-chloropyridazone-(6), and
   c. 2,3-dichloroallyl N,N-diisopropylthiolcarbamate 2,3,3-trichloroallyl N,N-diisopropylthiolcarbamate ethyl N-ethyl-N-cyclohexylthiolcarbamate, ethyl N,N-di-n-propylthiolcarbamate or n-propyl N-ethyl-N-n-butylthiolcarbamate.

2. A herbicide composition as claimed in claim 1, wherein compound (a) is O-(methylaminosulfonyl)-glycolic acid-N-isopropylanilide and compound (c) is 2,3-dichloroallyl N,N-diisopropylthiolcarbamate, 2,3,3-trichloroallyl N,N-diisopropylthiolcarbamate, or ethyl N-ethyl-N-cyclohexylthiolcarbamate.

3. A herbicide composition as claimed in claim 1, wherein compound (a) is O-(isopropylaminosulfonyl)-glycolic acid-N-butyn-1-yl-3-anilide or O-(methylaminosulfonyl)-glycolic acid-N-isopropylanilide, and compound (c) is ethyl N,N-di-n-propylthiolcarbamate or n-propyl N-ethyl-N-n-butylthiolcarbamate.

4. A herbicide composition as claimed in claim 1, wherein compound (a) is O-(methylaminosulfonyl)-glycolic acid hexamethylene amide, and compound (c) is 2,3-dichloroallyl N,N-diisopropylthiolcarbamate.

5. A herbicide composition as claimed in claim 1, wherein compound (a) is O-(methylaminosulfonyl)-glycolic acid-N-isopropylanilide, and compound (c) is 2,3-dichloroallyl N,N-diisopropylthiolcarbamate.

* * * * *